(12) United States Patent
Hwang et al.

(10) Patent No.: US 11,833,484 B2
(45) Date of Patent: Dec. 5, 2023

(54) APPARATUS FOR PREPARING OLIGOMER

(71) Applicant: LG CHEM, LTD., Seoul (KR)

(72) Inventors: Moon Sub Hwang, Daejeon (KR);
Jeong Seok Lee, Daejeon (KR); Hong Min Lee, Daejeon (KR); Jong Hun Song, Daejeon (KR); Kyung Seog Youk, Daejeon (KR); Min Ho Sun, Daejeon (KR); Hyun Seok Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/775,860

(22) PCT Filed: Aug. 12, 2021

(86) PCT No.: PCT/KR2021/010716
§ 371 (c)(1),
(2) Date: May 10, 2022

(87) PCT Pub. No.: WO2022/097886
PCT Pub. Date: May 12, 2022

(65) Prior Publication Data
US 2023/0041232 A1 Feb. 9, 2023

(30) Foreign Application Priority Data
Nov. 3, 2020 (KR) .................. 10-2020-0145157

(51) Int. Cl.
*B01J 8/02* (2006.01)
*B01D 5/00* (2006.01)
(Continued)

(52) U.S. Cl.
CPC .......... *B01J 8/0292* (2013.01); *B01D 5/0069* (2013.01); *B01D 19/0042* (2013.01);
(Continued)

(58) Field of Classification Search
CPC ...... B01D 5/00; B01D 5/0057; B01D 5/0069; B01D 19/00; B01D 19/0042; B01D 19/0063; B01D 19/0073; B01D 53/00; B01D 53/002; B01J 8/00; B01J 8/001; B01J 8/008; B01J 8/02; B01J 8/0292;
(Continued)

(56) References Cited

U.S. PATENT DOCUMENTS

2007/0249737 A1 10/2007 Miller et al.
2009/0087683 A1 4/2009 Shiraishi et al.

FOREIGN PATENT DOCUMENTS

CN   201609597 U   10/2010
CN   107973536 A   5/2018
(Continued)

*Primary Examiner* — Natasha E Young
(74) *Attorney, Agent, or Firm* — Bryan Cave Leighton Paisner LLP

(57) ABSTRACT

The present disclosure relates to an apparatus for preparing an oligomer, including: a reactor receiving a monomer stream and performing an oligomerization reaction to prepare a reaction product; a product discharge line for transferring a reaction product stream discharged from the reactor; and a bubble catcher provided in any area of the product discharge line to remove bubbles contained in the reaction product stream.

13 Claims, 4 Drawing Sheets

(51) Int. Cl.
*B01D 19/00* (2006.01)
*B01J 8/00* (2006.01)
*C07C 2/32* (2006.01)

(52) U.S. Cl.
CPC .......... *B01D 19/0063* (2013.01); *B01J 8/001* (2013.01); *B01J 8/008* (2013.01); *B01J 2208/0061* (2013.01); *B01J 2208/00938* (2013.01); *C07C 2/32* (2013.01)

(58) Field of Classification Search
CPC ...... B01J 19/00; B01J 19/0053; B01J 19/006; B01J 2208/00; B01J 2208/00008; B01J 2208/00539; B01J 2208/00548; B01J 2208/00557; B01J 2208/0061; B01J 2208/00796; B01J 2208/00938; B01J 2219/00; B01J 2219/00049; B01J 2219/00191; B01J 2219/00211; B01J 2219/00213; B01J 2219/00222; B01J 2219/00227; B01J 2219/00229; B01J 2219/00245; B01J 2219/00247; B01J 2219/00761; B01J 2219/00763; B01J 2219/00765; B01J 2219/00768; C07C 2/00; C07C 2/02; C07C 2/04; C07C 2/06; C07C 2/08; C07C 2/26; C07C 2/32; C07C 2/76; C07C 11/00; C07C 11/02; C07C 11/107; C07C 2531/00; C07C 2531/02; C07C 2531/12; C07C 2531/14
See application file for complete search history.

(56) References Cited

FOREIGN PATENT DOCUMENTS

| | | | |
|---|---|---|---|
| EP | 1777209 | A1 | 4/2007 |
| EP | 3345035 | A1 | 7/2018 |
| EP | 3345935 | A1 | 7/2018 |
| JP | 2006-272131 | A | 10/2006 |
| JP | 2006-272132 | A | 10/2006 |
| JP | 2009-511267 | A | 3/2009 |
| JP | 2009-511721 | A | 3/2009 |
| JP | 2019-517914 | A | 6/2019 |
| KR | 10-2002-0078883 | A | 10/2002 |
| KR | 10-2004-0099973 | A | 12/2004 |
| KR | 10-2006-0017847 | A | 2/2006 |
| KR | 10-1060383 | B1 | 8/2011 |
| KR | 10-2015-0042726 | A | 4/2015 |
| KR | 10-2017-0055452 | A | 5/2017 |
| KR | 10-1745896 | B1 | 6/2017 |
| KR | 10-2019-0011245 | A | 2/2019 |
| KR | 10-2019-0075572 | A | 7/2019 |
| WO | WO-2013168099 | A1 * | 11/2013 ............... B01D 1/00 |
| WO | 2017205071 | A1 | 11/2017 |

\* cited by examiner

【FIG. 1】
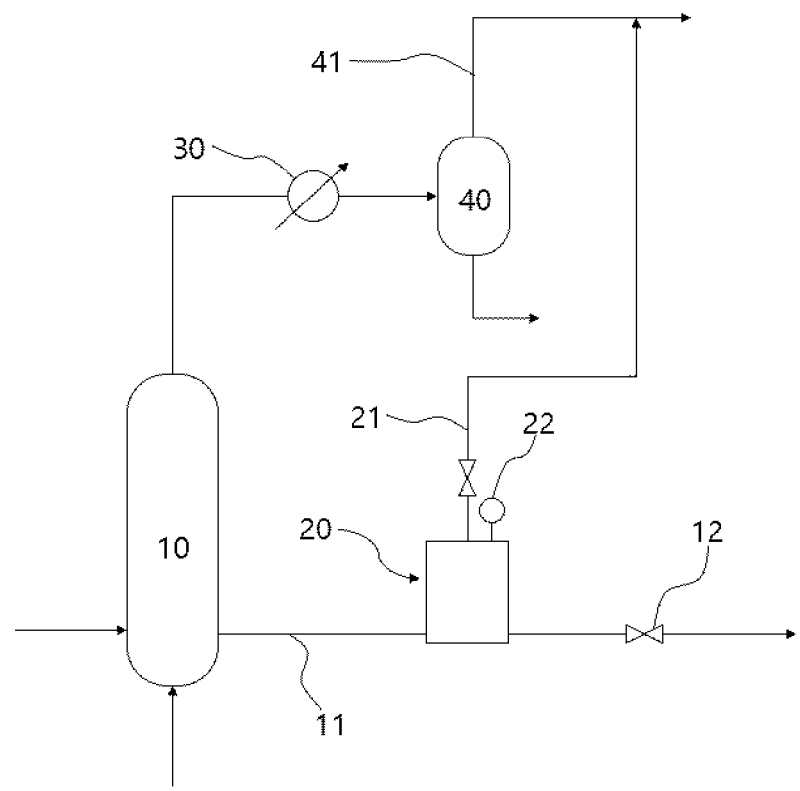
【FIG. 2】
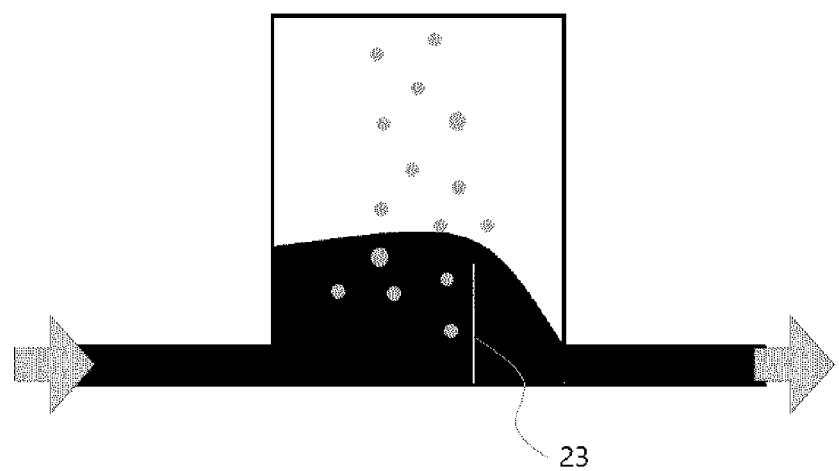

【FIG. 3】
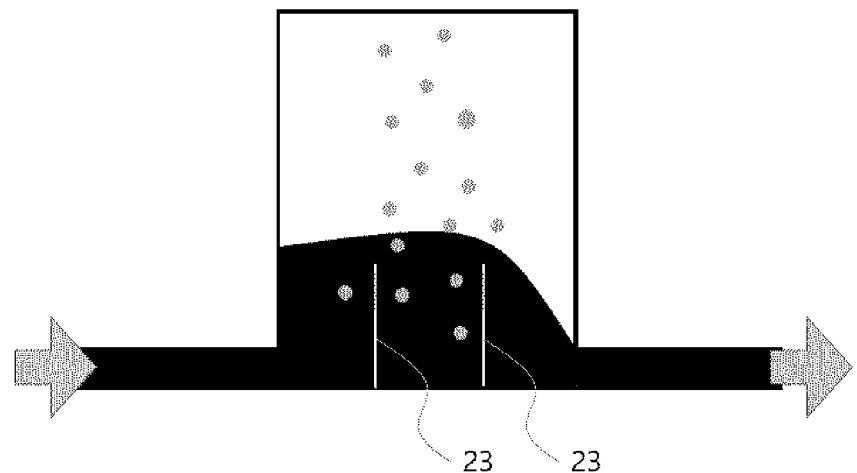
【FIG. 4】
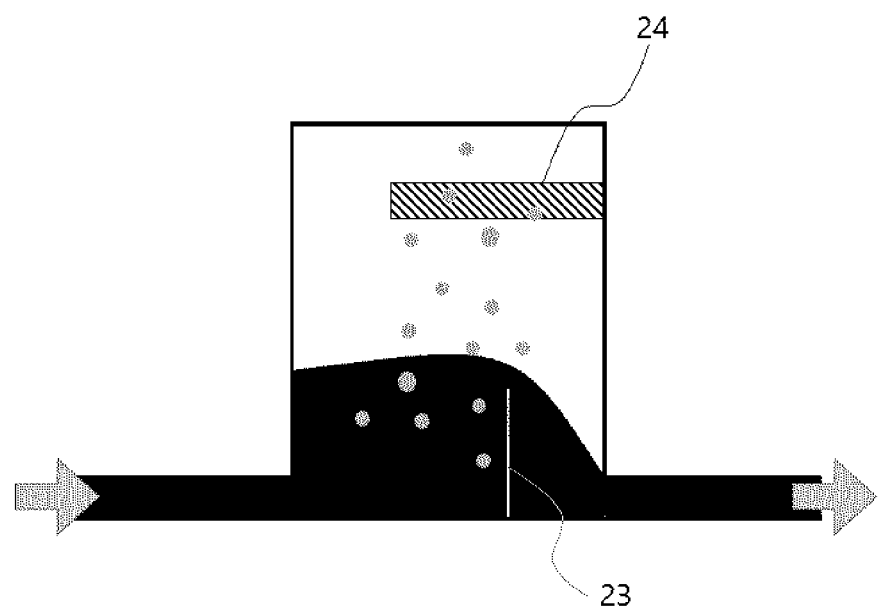

【FIG. 5】
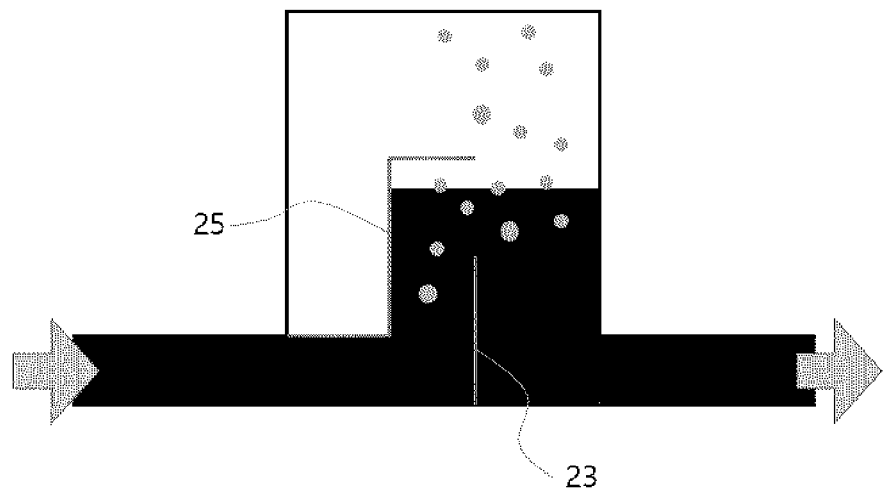
【FIG. 6】
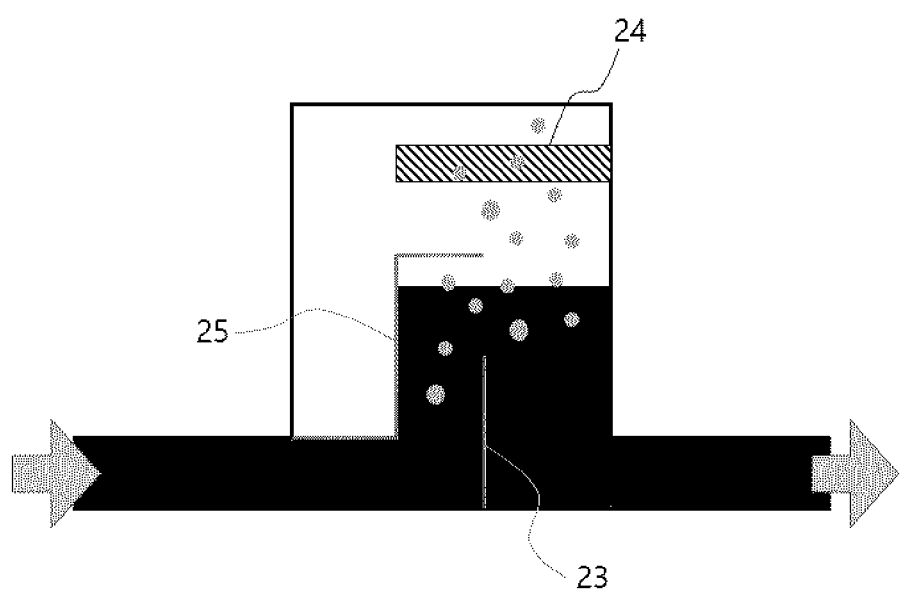

【FIG. 7】
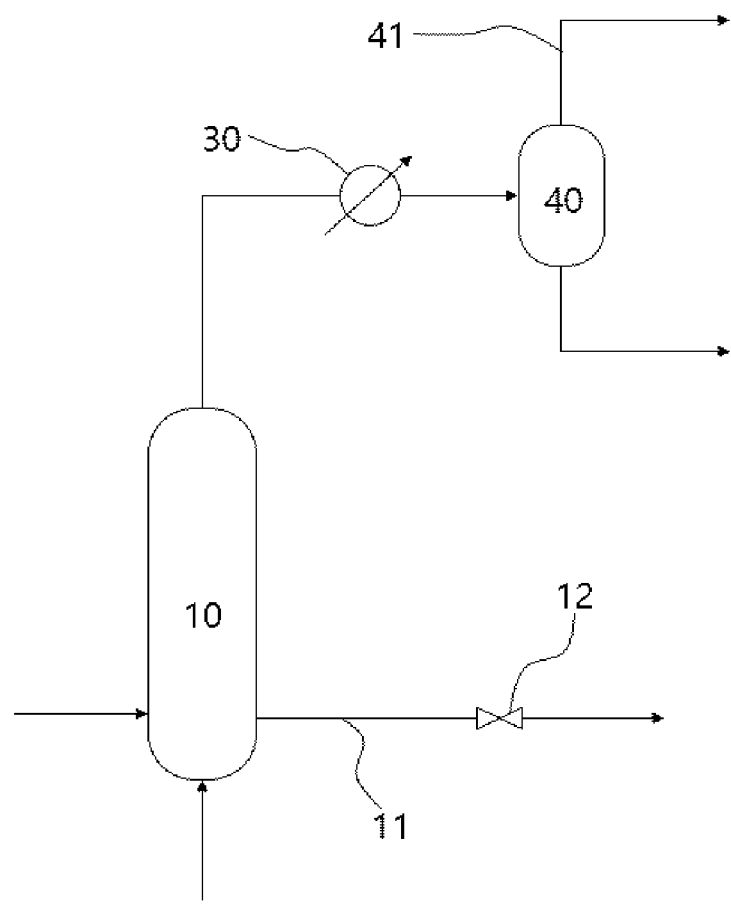

APPARATUS FOR PREPARING OLIGOMER

CROSS-REFERENCE TO RELATED APPLICATIONS

The present application is a National Phase entry pursuant to 35 U.S.C. § 371 of International Application No. PCT/KR2021/010716, now WO 2022/097886, filed on Aug. 12, 2021, and claims the benefit of and priority to Korean Patent Application No. 10-2020-0145157, filed on Nov. 3, 2020, the disclosure of which are incorporated by reference in their entirety for all purposes as if fully set forth herein.

TECHNICAL FIELD

The present invention relates to an apparatus for preparing an oligomer, and more particularly, to an apparatus for preparing an oligomer capable of preventing clogging of a level control valve provided in a product discharge line by separating bubbles contained in a reaction product stream discharged through the product discharge line using a bubble catcher during preparation of the oligomer.

BACKGROUND ART

α-olefins (alpha-olefins) are an important material used in comonomers, detergents, lubricants, plasticizers, etc., and have been commercially widely used. Among them, 1-hexene and 1-octene have been widely used as comonomers for controlling a density of polyethylene during preparation of linear low density polyethylene (LLDPE).

The α-olefins such as 1-hexene and 1-octene have been typically prepared by an oligomerization reaction of ethylene. The oligomerization reaction of the ethylene is performed by an oligomerization reaction (a trimerization reaction or a tetramerization reaction) of the ethylene in the presence of a catalyst using the ethylene as a reactant.

In the oligomerization reaction of the ethylene, an independent gas holdup ratio in a reactor is distributed in the range of 5% to 40% depending on a reaction condition. Therefore, a reaction product stream discharged from the reactor is present in a multi-phase including a liquid-phase and a gas-phase.

In this case, when the reaction product stream in which a gas and a liquid are mixed with each other is discharged through a product discharge line of the reactor, a choked flow phenomenon in which a discharge flow immediately after a level control valve provided in the product discharge line is congested to be subjected to strong resistance may occur. In addition, a flow before and after the level control valve is not smooth, and a congestion phenomenon of the polymer caused by a side reaction is added, which ultimately leads to a clogging phenomenon of the level control valve.

DISCLOSURE

Technical Problem

An object of the present invention is to provide an apparatus for preparing an oligomer capable of preventing clogging of a level control valve provided in a product discharge line of a reactor.

Technical Solution

In one general aspect, there is provided an apparatus for preparing an oligomer, including: a reactor receiving a monomer stream and performing an oligomerization reaction to prepare a reaction product; a product discharge line for transferring a reaction product stream discharged from the reactor; and a bubble catcher provided in an area of the product discharge line to remove bubbles contained in the reaction product stream.

Advantageous Effects

The apparatus for preparing an oligomer according to the present invention may include a bubble catcher in a product discharge line of the reactor to remove bubbles in the reaction product stream which is transferred through the product discharge line and in which the gas and the liquid are mixed with each other thereby making the flow of the reaction product stream in the product discharge line smooth and preventing clogging of the level control valve.

DESCRIPTION OF DRAWINGS

FIG. 1 is a process flow chart including an apparatus for preparing an oligomer according to an exemplary embodiment of the present invention.

FIGS. 2 to 6 illustrate flows of reaction product streams in a bubble catcher according to an exemplary embodiment of the present invention.

FIG. 7 is a process flow chart including an apparatus for preparing an oligomer according to Comparative Example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "upper portion" may refer to a portion corresponding to a height of 50% or more from a total height of the device in a container, and the term "lower portion" may refer to a portion corresponding to a height less than 50% from the total height of the device in the container.

In the present invention, the term "stream" may refer to a flow of a fluid in a process, or may refer to a fluid itself flowing in a pipe. Specifically, the "stream" may refer to both a fluid itself flowing in a pipe connecting respective devices and a flow of the fluid. In addition, the fluid may refer to a gas, a liquid, and the like. A case where the fluid contains a solid component is not excluded.

Hereinafter, the present invention will be described in more detail with reference to FIGS. 1 to 6 in order to assist in the understanding of the present invention.

According to the present invention, there is provided an apparatus for preparing an oligomer. As the apparatus for preparing an oligomer, there is provided an apparatus for preparing an oligomer, including: a reactor 10 receiving a monomer stream and performing an oligomerization reaction to prepare a reaction product; a product discharge line 11 for transferring a reaction product stream discharged from the reactor 10; and a bubble catcher 20 provided in any area of the product discharge line 11 to remove bubbles contained in the reaction product stream.

According to an exemplary embodiment of the present invention, the reactor 10 may prepare a reaction product including a desired oligomer product by receiving a monomer stream and performing an oligomerization reaction.

The oligomerization reaction in the reactor 10 may be performed in a liquid-phase reaction medium. The liquid-phase reaction medium may be supplied to a lower portion of a side surface of the reactor 10, and may include one or more selected from the group consisting of a solvent, a catalyst, and a cocatalyst.

The solvent may include, for example, one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene. In some cases, a mixture of two or more of those described above may be used as the solvent.

The catalyst may include, for example, a transition metal source. The transition metal source may be, for example, a compound including one or more selected from the group consisting of chromium (III) acetylacetonate, chromium (III) chloride tetrahydrofuran, chromium (III) 2-ethylhexanoate, chromium (III) tris(2,2,6,6-tetramethyl-3,5-heptanedionate), chromium (III) benzoylacetonate, chromium (III) hexafluoro-2,4-pentanedionate, chromium (III) acetate hydroxide, chromium (III) acetate, chromium (III) butyrate, chromium (III) pentanoate, chromium (III) laurate, and chromium (III) stearate.

The cocatalyst may include, for example, one or more selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, modified methylaluminoxane, and borate.

The monomer may include ethylene. Specifically, a monomer stream containing ethylene monomers is supplied to reactor 10 and is subjected to an oligomerization reaction, such that a desired oligomer, α-olefin, may be prepared. In this case, the oligomerization reaction is performed in a reaction medium of lower to central areas of the reactor 10, and the oligomerization reaction of the monomers may be performed in a liquid state in which the monomers are dissolved in a solvent in the presence of a catalyst. The oligomerization reaction may refer to a reaction in which a monomer is polymerized. The oligomerization reaction is called trimerization or tetramerization depending on the number of monomers to be polymerized, and these are collectively called multimerization.

α-olefins are an important material used in comonomers, detergents, lubricants, plasticizers, etc., and have been commercially widely used. Among them, 1-hexene and 1-octene have been widely used as comonomers for controlling a density of polyethylene during preparation of linear low density polyethylene (LLDPE). The α-olefin such as 1-hexene and 1-octene may be prepared by, for example, a trimerization reaction or tetramerization reaction of ethylene.

The reactor 10 may include, for example, one or more reactors selected from the group consisting of a continuous stirred-tank reactor, a plug flow reactor, and a bubble column reactor. As a specific example, the reactor may be a bubble column reactor.

The oligomerization reaction which is performed by a monomer stream supplied to the reactor 10 may be performed at a temperature of 10° C. to 180° C., 30° C. to 150° C., or 50° C. to 120° C. In addition, the oligomerization reaction may be performed under a pressure of 10 bar·g to 70 bar·g, 20 bar·g to 65 bar·g, or 20 bar·g to 40 bar·g. When the ethylene is oligomerized within the temperature range and the pressure range described above, a selectivity to a desired α-olefin may be excellent, an amount of polymer by-products may be decreased, an operational efficiency of a continuous process may be increased, and costs may be reduced.

The monomer stream may be supplied to the reactor 10 in a gas-phase through a monomer supply line provided at a lower portion of the reactor 10. In this case, a gas-phase monomer stream is dispersed into gas through a porous dispersion plate installed in a lower portion of the reactor 10, introduced into the liquid-phase reaction medium containing a solvent, and naturally mixed by a dispersed force, which may cause an oligomerization reaction. In this case, a ratio of independent gas holdups in the reactor 10 is distributed in the range of 5% to 40% depending on a reaction condition. Therefore, a reaction product is present in a multi-phase including a liquid-phase and a gas-phase.

The reaction product generated in the reactor 10 may be discharged from the reactor 10 through the product discharge line 11. In this case, when the reaction product stream in which gas and liquid are mixed with each other is discharged through a product discharge line 11 of the reactor 10, a choked flow phenomenon may occur where a discharge flow immediately after the level control valve 12 provided in the product discharge line 11 becomes congested and is subjected to strong resistance. In addition, a flow before and after the level control valve 12 is not smooth, and a congestion phenomenon of the polymer caused by a side reaction is added, which ultimately leads to a clogging of the level control valve 12.

To this end, in the present invention, a bubble catcher 20 may be provided in any area of the product discharge line 11 to remove bubbles contained in the reaction product stream, thereby making a flow smooth.

According to an exemplary embodiment of the present invention, the bubble catcher 20 may further include a pressure gauge 22 provided therein. The bubbles ascend in the bubble catcher 20, and the bubbles congested at an upper portion of the bubble catcher 20 may be discharged to a gas recovery line 21 by monitoring the pressure gauge 22 if necessary. Specifically, the pressure gauge 22 may measure an internal pressure of the bubble catcher 20 changed depending on the bubbles that ascend and congested inside the bubble catcher 20, determine that the bubbles have sufficiently filled an internal space of the bubble catcher 20 when a difference between the internal pressure of the bubble catcher 20 and a pressure of the reactor 10 is reduced to, for example, 1 bar·g or less, 0.1 bar·g to 1 bar·g, or 0.3 bar·g to 1 bar·g, and discharge the bubbles congested through the gas recovery line 21 connected from above the bubble catcher 20 to the bubble catcher 20 so that the filled bubbles do not interfere with a flow of a liquid-phase reaction product. In this case, a block valve may be provided in the gas recovery line 21 to open or close through the monitoring of the pressure gauge 22 to discharge the bubbles congested in the bubble catcher 20, if necessary.

According to an exemplary embodiment of the present invention, the bubble catcher 20 may further include a baffle 23 provided therein. Specifically, an inlet and an outlet of the bubble catcher 20 may be formed at lower portions of both side surfaces of the bubble catcher 20, respectively, and the reaction product stream may be supplied to the inlet of the bubble catcher 20, be transferred inside the bubble catcher 20, and be discharged to the outlet of the bubble catcher 20. Here, the baffle 23 may be provided vertically from a bottom surface of the bubble catcher 20, through which the reaction product stream may flow with curves, not straight from the inlet to the outlet of the bubble catcher 20. In this case, the path through which the reaction product stream is transferred is longer due to the baffle 23, such that a residence time in the bubble catcher 20 is increased, the bubbles are raised, and the liquid-phase reaction product flows towards the outlet, which may make it easier to remove the bubbles contained in the reaction product stream.

The number of baffles 23 provided in the bubble catcher 20 may be one to three, one or two, or one. As a specific example, the number of baffles 23 provided in the bubble catcher 20 may be one. In this case, the bubbles may be sufficiently discharged to a space of an upper area without significant congestion of a flow of a reaction product stream in which a gas and a liquid are mixed with each other. In addition, a fouling phenomenon of the apparatus by the polymer, which is a by-product that may be contained in the reaction product stream may be minimized.

The bubble catcher 20 may further include a guide part 25 guiding the flow of the reaction product in the bubble catcher 20 toward an outlet. Specifically, the guide part 25 may be formed to be spaced apart from the bottom surface of the bubble catcher 20 and the baffle 23 by a predetermined interval so that the flow of the reaction product in the bubble catcher 20 is guided toward the outlet. For example, the guide part 25 may extend horizontally from a lower portion of an inner wall of an inlet side bubble catcher 20, may extend vertically from the horizontally extending end in an upward direction, and may extend horizontally again from the vertically extending end to be connected to an area between the baffle 23 and a demister 24 to be described later. The guide part 25 may guide the reaction product transferred in the bubble catcher 20 from the inlet to the outlet of the bubble catcher 20 and at the same time, prevent a vortex from being generated when a flow direction of the reaction product stream transferred in the bubble catcher 20 is changed by the baffle 23, thereby minimizing contamination of the gas recovery line 21 caused by a liquid and a polymer entrained with the bubbles.

According to an exemplary embodiment of the present invention, the bubble catcher 20 may further include a demister 24 provided therein. Specifically, the demister 24 is a device for separating the liquid-phase reaction product that ascends with the bubbles in the bubble catcher 20, and may be provided in an upper area of the bubble catcher 20.

The demister 24 may be formed in an independent gas space above an area where the reaction product stream is transferred, inside the bubble catcher 20. As a specific example, the demister 24 may be formed in an upper area corresponding to an area where the flow of the reaction product stream is changed due to the baffle 23. In this case, when the bubbles contained in the reaction product stream are discharged and ascend to the upper area while the flow is changed due to the baffle 23, it may be easy to remove the liquid-phase reaction product entrained with the bubbles by using the demister 24.

According to an exemplary embodiment of the present invention, the level control valve 12 for controlling a level of a liquid-phase, that is, a level of the reaction medium, in order to constantly maintain a catalytic reaction in the reactor 10 may be provided in any area of the product discharge line 11. For example, the level control valve 12 may control a flow rate of the reaction product stream discharged through the product discharge line 11 to constantly maintain a level of the liquid-phase in the reactor 10.

In this case, in the product discharge line 11, the bubble catcher 20 may be provided in front of the level control valve 12 based on a flow direction of the reaction product stream. Therefore, the gas in the reaction product stream in which the gas and the liquid are mixed with each other is removed, and the reaction product stream from which the gas component is removed passes through the level control valve 12 to prevent a discharge flow immediately after the level control valve 12 from being congested, thereby making the flow smooth and preventing a clogging phenomenon of the level control valve 12.

The reaction product stream passing through the level control valve 12 may be supplied to a purification part, and a desired oligomer may be separated and purified through a general separation and purification process of the reaction product stream, and be then commercialized.

According to an exemplary embodiment of the present invention, a gas-phase stream containing monomers unreacted during the oligomerization reaction in the reactor 10 may be discharged from an upper portion of the reactor 10. The gas-phase stream discharged from the upper portion of the reactor 10 is condensed while passing through a condenser 30, and may be supplied to a gas-liquid separation device 40. For example, the gas-liquid separation device 40 may be a flash drum.

In the gas-liquid separation device 40, a condensate condensed and a non-condensate while passing through the condenser 30 may be separated. In this case, the non-condensate may be discharged as a gas-phase stream from the gas-liquid separation device 40 through an upper discharge line 41 of the gas-liquid separation device 40. Further, the gas-phase stream discharged from the gas-liquid separation device 40 contains unreacted monomers, and may be removed or circulated to the reactor 10 to participate in the oligomer reaction again.

In the gas-liquid separation device 40, the condensate may be discharged as a liquid stream from the gas-liquid separation device 40 through a lower discharge line of the gas-liquid separation device 40. Further, the liquid-phase stream discharged from the gas-liquid separation device 40 contains the reaction medium, and may be removed or circulated to the reactor 10 to be reused.

According to an exemplary embodiment of the present invention, the gas recovery line 21 of the bubble catcher 20 may extend from the bubble catcher 20 and join in the upper discharge line 41 of the gas-liquid separation device 40. Specifically, the bubbles separated from the reaction product stream discharged through the gas recovery line 21 of the bubble catcher 20 contain a gas-phase monomer, and have a component similar to that of the gas-phase stream discharged from the gas-liquid separation device 40, and thus, may join and be removed in the upper discharge line 41 of the gas-liquid separation device 40 or be circulated to the reactor 10.

The apparatus for preparing an oligomer according to the present invention has been described hereinabove and illustrated in the drawings, but only essential components for understanding the present invention have been described above and illustrated in the drawings, and in addition to the processes and the devices described above and illustrated in the drawings, processes and devices that are not separately described and illustrated may be appropriately applied and used to implement the apparatus for preparing an oligomer according to the present invention.

Hereinafter, the present invention will be described in more detail by Examples. However, the following Examples are provided in order to exemplify the present invention, it is apparent to those skilled in the art that various modifications and alterations may be made without departing from the scope and spirit of the present invention, and the scope of the present invention is not limited to these Examples.

EXAMPLE

Example 1

As illustrated in FIG. 1, an ethylene monomer and a reaction medium were supplied to a bubble column reactor 10, and were subjected to an oligomerization reaction to prepare a reaction product.

A gas-phase stream discharged from the reactor 10 was supplied to the gas-liquid separation device 40 through the condenser 30, and a gas-phase stream containing a non-condensate was discharged through the upper discharge line 41 of the gas-liquid separation device 40.

A reaction product stream discharged from the reactor 10 was discharged through the product discharge line 11, and bubbles in the reaction product stream were removed while the reaction product stream passes through the bubble catcher 20 including one baffle 23 in a flow as illustrated in FIG. 2. In this case, it was confirmed that a content of a gas-phase component in the reaction product stream supplied to the bubble catcher 20 was about 15% by weight based on the total content of the reaction product stream, and it was confirmed that a content of a gas-phase component in the reaction product stream passing through the bubble catcher 20 is 3% by weight or less based on the total content of the reaction product stream.

The reaction product discharged from the bubble catcher 20 passed through the level control valve 12 and was then discharged. In this case, an internal pressure of the bubble catcher 20 was monitored through the pressure gauge 22, and when a difference between the internal pressure of the bubble catcher 20 and a pressure of the reactor 10 is reduced to 1 bar·g or less, bubbles congested in an upper area of the bubble catcher 20 were discharged through the gas recovery line 21 and joined in the upper discharge line 41 of the gas-liquid separation device 40.

As a result, it appeared that a cleaning cycle at which cleaning needs to be performed due to occurrence of clogging of the level control valve 12 provided behind the bubble catcher 20 was 8 hours or more.

Example 2

The same processes as Example 1 were performed except that the bubbles in a reaction product stream discharged through the product discharge line 11 were removed while the reaction product stream passes through the bubble catcher 20 including two baffles 23 in a flow as illustrated in FIG. 3. In this case, it was confirmed that a content of a gas-phase component in the reaction product stream supplied to the bubble catcher 20 is about 15% by weight based on the total content of the reaction product stream, and it was confirmed that a content of a gas-phase component in the reaction product stream passing through the bubble catcher 20 is 3% by weight or less based on the total content of the reaction product stream.

As a result, it appeared that a cleaning cycle at which cleaning needs to be performed due to occurrence of clogging of the level control valve 12 provided behind the bubble catcher 20 was 8 hours or more, and it appeared that the number of baffles 23 was increased, such that amounts of a liquid and a polymer entrained to flowing out to the gas recovery line 21 were slightly increased compared to Example 1.

Example 3

The same processes as Example 1 were performed except that the bubbles in a reaction product stream discharged through the product discharge line 11 were removed while the reaction product stream passes through the bubble catcher 20 including one baffle 23 and the demister 24 in a flow as illustrated in FIG. 4. In this case, it was confirmed that a content of a gas-phase component in the reaction product stream supplied to the bubble catcher 20 is about 15% by weight based on the total content of the reaction product stream, and it was confirmed that a content of a gas-phase component in the reaction product stream passing through the bubble catcher 20 is 3% by weight or less based on the total content of the reaction product stream.

As a result, it appeared that a cleaning cycle at which cleaning needs to be performed due to occurrence of clogging of the level control valve 12 provided behind the bubble catcher 20 was 8 hours or more, and it appeared that due to the demister 24, amounts of a liquid and a polymer entrained to flowing out to the gas recovery line 21 were decreased compared to Example 1.

Example 4

The same processes as Example 1 were performed except that the bubbles in a reaction product stream discharged through the product discharge line 11 were removed while the reaction product stream passes through the bubble catcher 20 including one baffle 23 and the guide part 25 in a flow as illustrated in FIG. 5. In this case, it was confirmed that a content of a gas-phase component in the reaction product stream supplied to the bubble catcher 20 is about 15% by weight based on the total content of the reaction product stream, and it was confirmed that a content of a gas-phase component in the reaction product stream passing through the bubble catcher 20 is 3% by weight or less based on the total content of the reaction product stream.

As a result, it appeared that a cleaning cycle at which cleaning needs to be performed due to occurrence of clogging of the level control valve 12 provided behind the bubble catcher 20 was 8 hours or more, and it appeared that due to the guide part 25, amounts of a liquid and a polymer entrained to flowing out to the gas recovery line 21 were decreased compared to Example 1.

Example 5

The same processes as Example 1 were performed except that the bubbles in a reaction product stream discharged through the product discharge line 11 were removed while the reaction product stream passes through the bubble catcher 20 including one baffle 23, the demister 24, and the guide part 25 in a flow as illustrated in FIG. 6. In this case, it was confirmed that a content of a gas-phase component in the reaction product stream supplied to the bubble catcher 20 is about 15% by weight based on the total content of the reaction product stream, and it was confirmed that a content of a gas-phase component in the reaction product stream passing through the bubble catcher 20 is 3% by weight or less based on the total content of the reaction product stream.

As a result, it appeared that a cleaning cycle at which cleaning needs to be performed due to occurrence of clogging of the level control valve 12 provided behind the bubble catcher 20 was 8 hours or more, and it could be confirmed that one baffle 23 was used, and the demister 24 and the guide part 25 were further provided to significantly decrease amounts of a liquid and a polymer entrained in the bubble catcher 20 flowing out to the gas recovery line 21 compared to Examples 1 to 4, such that clogging of the gas recovery line 21 was prevented and thus, an operation was further stabilized.

COMPARATIVE EXAMPLE

Comparative Example 1

As illustrated in FIG. 7, an ethylene monomer and a reaction medium were supplied to a bubble column reactor 10, and were subjected to an oligomerization reaction to prepare a reaction product.

The gas-phase stream discharged from the reactor 10 was supplied to the gas-liquid separation device 40 through the condenser 30, and the gas-phase stream containing non-condensate was discharged through the upper discharge line 41 of the gas-liquid separation device 40.

A reaction product stream discharged from the reactor 10 was discharged through the product discharge line 11 provided with the level control valve 12. In this case, it was confirmed that a content of a gas-phase component in the reaction product stream was about 15% by weight based on the total content of the reaction product stream.

As a result, it could be confirmed that a cleaning cycle at which cleaning needs to be performed due to occurrence of clogging of the level control valve 12 provided behind the bubble catcher 20 was 4 hours or less, which was significantly decreased compared to Examples 1 to 5.

The invention claimed is:

1. An apparatus for preparing an oligomer, comprising:
a reactor receiving a monomer stream and performing an oligomerization reaction to prepare a reaction product;
a product discharge line for transferring a reaction product stream discharged from the reactor; and
a bubble catcher provided in an area of the product discharge line to remove bubbles contained in the reaction product stream,
wherein the bubble catcher further includes one or more baffle(s) provided therein.

2. The apparatus for preparing an oligomer of claim 1, wherein a monomer included in the monomer stream comprises an ethylene monomer.

3. The apparatus for preparing an oligomer of claim 1, further comprising a level control valve provided in the product discharge line.

4. The apparatus for preparing an oligomer of claim 3, wherein the bubble catcher is provided between the reactor and the level control valve.

5. The apparatus for preparing an oligomer of claim 1, wherein the one or more baffle(s) are provided perpendicular to a flow direction of the reaction product stream in the bubble catcher.

6. The apparatus for preparing an oligomer of claim 1, wherein the number of baffle(s) is one to three.

7. The apparatus for preparing an oligomer of claim 6, wherein the number of baffle(s) is one.

8. The apparatus for preparing an oligomer of claim 1, wherein the bubble catcher further includes a guide part for guiding the flow of the reaction product in the bubble catcher toward an outlet.

9. The apparatus for preparing an oligomer of claim 1, wherein the bubble catcher further includes a demister provided therein.

10. The apparatus for preparing an oligomer of claim 9, wherein the demister is provided in an upper area of the bubble catcher.

11. The apparatus for preparing an oligomer of claim 1, further comprising a pressure gauge in the bubble catcher to monitor the bubbles ascended and congested in an upper portion of the bubble catcher for discharging.

12. The apparatus for preparing an oligomer of claim 11, further comprising:
a condenser through which a first gas-phase stream discharged from an upper portion of the reactor passes, and
a gas-liquid separation device that discharges a second gas-phase stream through an upper discharge line.

13. The apparatus for preparing an oligomer of claim 12, further comprising a gas recovery line connected from above the bubble catcher,
wherein the gas recovery line extends from the bubble catcher and joins in an upper discharge line of the gas-liquid separation device.

* * * * *